United States Patent [19]

Ben-Nun

[11] Patent Number: 5,976,543
[45] Date of Patent: Nov. 2, 1999

[54] **12-KDA PROTEIN DERIVED FROM *M. TUBERCULOSIS* USEFUL FOR TREATMENT OF AUTOIMMUNE DISEASES**

[75] Inventor: Avraham Ben-Nun, Yavne, Israel

[73] Assignee: Yeda Research and Development Co., Ltd., Rehovot, Israel

[21] Appl. No.: 08/849,377

[22] PCT Filed: Dec. 4, 1995

[86] PCT No.: PCT/US95/16444

§ 371 Date: Aug. 1, 1997

§ 102(e) Date: Aug. 1, 1997

[87] PCT Pub. No.: WO96/17864

PCT Pub. Date: Jun. 13, 1996

[30]   Foreign Application Priority Data

Dec. 4, 1994 [IL] Israel ......................................... 111865

[51] Int. Cl.$^6$ .......................... A61K 39/04; A61K 38/03; C07K 14/35
[52] U.S. Cl. .................... 424/190.1; 424/234.1; 424/184.1; 424/185.1; 424/248.1; 530/300; 530/350; 530/412; 530/413; 530/326; 530/417; 514/2
[58] Field of Search ............... 424/248.1, 234.1, 424/184.1, 185.1, 190.1; 530/300, 350, 412, 413, 326, 417; 514/2

[56]   References Cited

U.S. PATENT DOCUMENTS 4,879,213 11/1989 Fox et al. .

OTHER PUBLICATIONS

A. Ben–Nun et al., "A 12–KDA Protein of Mycobacterium Tuberculosis Protects Mice Against Experimental Autoimmune Encephalomyelitis." J. Immul., vol. 154, No. 6, pp. 2939–2948 (Mar. 15, 1995).
F. Mor et al., "T Cells in the Lesion of Experimental Autoimmune Encephalomyelitis." J. Clin. Invest., vol. 90, No. 6, pp. 2447–2455 (Dec. 1992).
A. Ben–Nun et al., "Protection Against Autoimmune Disease by Bacterial Agents II. PPD and Pertussis Toxin as Proteins Active in Protecting Mice Against Expiremental Autoimmune Encephalomyelitis." Eur. J. Immunol., vol. 23, No. 3, pp. 689–696 (1993).
Raines in Handbook of Clinical Neurology 3 (47): 429–466, 1985.
Weiner et al. Science 1993 259, 1321–1324.
Barnes et al. J. Immunol. 1992. vol. 148, No. 6, 1835–1840.
Deutscher Methods in Enzymology, vol. 182, pp. 80–81.
Burgess et al., J. Cell Biol. 1990 vol. 111, 2129–2138.
Lazar et al., Mol. Cell. Biol. 1988 vol. 8 (3), 1247–1252.
Vijay Mehra et al., "A Major T Cell Antigen of Mycobacterium Leprae Is a 10–kD Heat–Shock Cognate Protein", J. Exp. Med., vol. 175, pp. 275–284, Jan. 1992.
Thomas M. Shinnick et al., "The Mycobacterium Tuberculosis BCG–a protein has homology with the *Escherichia coli* GroES Protein", Nucleic Acids Research, vol. 17, No. 3, p. 1254, 1989.
Ryuji Yamaguchi et al., "Immunogenic Protein MPB57 From Mycobacterium Bovis BCG: Molecular Cloning, Nucleotide Sequence and Expression", FEBS Lett., vol. 240, No. 1,2, pp. 115–117, Nov., 1988.
Klaus Hempel et al., "Unresponsiveness to Experimental Allergic Encephalomyelitis in Lewis Rats Pretreated With Complete Freund's Adjuvant", Int. Arch. Allergy Appl. Immunol., vol. 76, pp. 193–199, 1985.
Dan Lehmann et al., "Bacterial Agents Protect Against Autoimmune Disease. I. Mice Pre–exposed to Bordetella Pertussis or Mycobacterium Tuberculosis are Highly Refractory to Induction of Experimental Autoimmune Encephalomyelitis", Journal of Autoimmunity, vol. 5, pp. 675–690, 1992.
Robert P. Lisak et al., "Mycobacterial Suppression of Delayed Hypersensitivity in Experimental Allergic Encephalomyelitis", Proc. Soc. Exp. Biol. Med., vol. 128, pp. 214–218, 1968.
Iain A.M. MacPhee et al., "Studies on the Refractoriness to Reinduction of Experimental Allergic Encephalomyelitis in Lewis Rats That Have Recovered From One Episode of the Disease", Journal of Neuroimmunology, vol. 27, pp. 9–19, 1990.

*Primary Examiner*—Anthony C. Caputa
*Assistant Examiner*—Khalid Masood
*Attorney, Agent, or Firm*—Browdy and Neimark

[57]   ABSTRACT

Disclosed is a 12-kDa PPD protein isolated and purified from the purified protein derivative, the major fraction of *Mycobacterium tuberculosis* that protects mice against the induction of experimental autoimmune encephalomyelitis (EAE), and salts, functional derivatives, analogs and active fractions thereof, and pharmaceutical compositions comprising them for the treatment of autoimmune diseases.

10 Claims, 8 Drawing Sheets

STIMULATION OF:
DSP CELLS — — —
DSBP CELLS — — —
NSPLP CELLS — — —

| | | |
|---|---|---|
| 12 kDa PPD PROTEIN | | A K V N I K P L E D K I L V Q A N |
| Mt. 10 kda BCG-a PROTEIN | | V A K V N I K P L E D K I L V Q A N |
| M. BOVIS 10 kda | | V A K V N I K P L E D K I L V Q A N |
| M. LEPRAE 10 kda | | V A K V K I K P L E D K I L V Q A G |
| E. COLI GroES | | M N I R P L H D R V I V K R K |

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 18 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Val Ala Lys Val Asn Ile Lys Pro Leu Glu Asp Lys Ile Leu Val Gln
1               5                   10                  15

Ala Asn (2) INFORMATION FOR SEQ ID NO:2:

(i) SEQUENCE CHARACTERISTICS:
       (A) LENGTH: 18 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Val Ala Lys Val Lys Ile Lys Pro Leu Glu Asp Lys Ile Leu Val Gln
1               5                   10                  15

Ala Gly (2) INFORMATION FOR SEQ ID NO:3:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Met Asn Ile Arg Pro Leu His Asp Arg Val Ile Val Lys Arg Lys
1               5                   10                  15

# 12-KDA PROTEIN DERIVED FROM M. TUBERCULOSIS USEFUL FOR TREATMENT OF AUTOIMMUNE DISEASES

This application is a 371 of PCT/US96/16444 filed Dec. 4, 1995 which claims priority to foreign application Israel 111865 filed Dec. 4, 1994.

FIELD OF THE INVENTION

The present invention relates to agents that may be used for the treatment of autoimmune diseases, and more particularly to a protein having a molecular weight of about 12-kDa isolated and purified from the purified protein derivative (PPD), the major fraction of *Mycobacterium tuberculosis* (Mt) that protects mice against the induction of experimental autoimmune encephalomyelitis (EAE), and to salts, functional derivatives, analogs and active fractions thereof.

ABBREVIATIONS

In the specification, the following abbreviations will be used: Ag, antigen; EAE, experimental autoimmune encephalomyelitis; PPD, purified protein derivative; MBP, myelin basic protein; Mt, *Mycobacterium tuberculosis*; PLP, proteolipid protein; RPLC, reverse phase high-pressure liquid chromatography; CFA, complete Freund's adjuvant; IFA, incomplete Freund's adjuvant; SDS-PAGE, sodium dodecyl sulphate polyacrylamide gel electrophoresis; hsp, heat shock protein.

BACKGROUND OF THE INVENTION

Increasing evidence suggests that infectious agents can affect the development of autoimmune diseases. Viruses have been most often implicated in the etiology of autoimmune diseases, although bacteria may also be involved: streptococcal infection may lead to rheumatic fever and myocarditis, Mycoplasma arthriditis or its toxins can cause arthritis in mice or rats, and arthritis has also been associated with reactivity to mycobacterial antigens, both in humans and rats. However, several reports indicate that viruses and bacteria may also enhance the natural propensity of mice to become resistant to an autoimmune disease. Thus, nonobese diabetic mice infected with lymphocytic choriomeningitis virus become resistant to the development of insulin-dependent diabetes mellitus, and mice infected with lactic dehydrogenase virus are refractory to the development of experimental autoimmune encephalomyelitis (EAE). Similarly, bacteria may also be involved in conferring resistance to autoimmune diseases, as demonstrated in a previous study by the present inventor (Lehman and Ben-Nun, 1992).

EAE is an autoimmune disease of the central nervous system (CNS) that is caused by CD4+ T lymphocytes specific for myelin antigens, such as MBP or PLP (Ben-Nun and Lando, 1983). In SJL/J mice, the disease can be induced by injecting the animals with CNS homogenate, MBP or PLP, or with peptides derived therefrom (Raine, 1984). However, disease induction is dependent on the presence of immunoadjuvant in the inoculum. Mt is routinely used as the immunopotentiating agent in the induction of experimental autoimmune diseases. However, its mode of action in enhancing the development of the disease remains unclear. Although controversial data were obtained, there is an indication that Mt can also protect Lewis rats against the induction of an autoimmune disease (Lisak and Kies, 1968; MacPhee and Mason, 1990; Hempel et al., 1985). The inventor recently analyzed the effect of Mt and other bacteria on EAE in SJL/J mice, and observed that mice pre-exposed to Mt acquired long-lasting resistance to EAE, even when the bacteria were administered as an aqueous preparation, rather than as an emulsion in IFA. This study clearly demonstrated that Mt can not only promote the development of EAE, but can also protect against the disease, depending on the time of exposure to the bacteria (Lehman and Ben-Nun, 1992). Because effective protection was obtained with non-pathogenic bacterial preparations (heat-killed bacteria), it was speculated that immunity against a particular component(s) of Mt may be sufficient to confer resistance against induction of an autoimmune disease. Accordingly, it was recently demonstrated by the inventor that PPD is the major fraction of Mt which confers on mice resistance to induction of EAE (Ben-Nun et al., 1993). The protection observed following immunization with PPD was not a simple consequence of a non-specific effect on the immune balance, as other immunogens, both bacterial and non-bacterial, had only marginal or no protective effect.

It should be noted that EAE is the well established and widely accepted animal model for studying the effects of various agents which may be implicated in human autoimmune diseases in general, and particularly multiple sclerosis, rheumatoid arthritis, systemic lupus erythematosus, insulin-dependent diabetes mellitus and graft-versus-host disease. Thus, an agent found to be capable of eliciting a protective effect against EAE in animals such as mice or rats, is also considered to be an agent capable of eliciting protection against autoimmune diseases in humans.

SUMMARY OF THE INVENTION

The present invention is based on the identification of the major PPD component that confers resistance against EAE. This component, the 12-kDa protein of the invention, was isolated and purified by a procedure in which the PPD was fractionated by RPLC, the resulting fractions were then evaluated for their effect on the development of EAE, and a protein of approximate m.w. of 12-kDa was identified and purified from one of the two highly protective PPD fractions by rechromatography and preparative gel electrophoresis. This purified 12-kDa protein, which has also been partially sequenced, is capable of protecting mice against the development of EAE.

Accordingly, the present invention provides a protein derived from the "Purified Protein Derivative" (PPD) of *Mycobacterium tuberculosis* (herein 12-kDa PPD protein) capable of protecting mice against EAE and to stimulate PPD-specific T lymphocytes, said protein having a molecular weight of about 12-kDa when analysed by SDS-PAGE under reducing conditions, and comprising the follow ing amino acid sequence obtained by N-terminal analysis:

Ala-Lys-Val-Asn-Ile-Lys-Pro-Leu-Glu-Asp-Lys-Ile-Leu-Val-Gln-Ala-Asn (residues 2–18 of SEQ ID NO:1)
and salts, functional derivatives, analogs and active fractions thereof and mixtures of any of the foregoing.

In one preferred embodiment, the invention relates to the 12-kDa PPD protein in substantially purified form.

The present invention also provides pharmaceutical compositions comprising he 12-kDa PPD protein, salts, functional derivatives, analogs or active fractions thereof or mixtures of any of the foregoing, according to the invention, and a pharmaceutical acceptable carrier, diluent or excipient. These pharmaceutical compositions may be used against autoimmune diseases in general, and in particular against diseases such as multiple sclerosis, rheumatoid arthritis, systemic lupus erythematosus, insulin-dependent diabetes mellitus and graft-versus-host disease. Likewise, the use of the protein, salts, functional derivatives, analogs or active fractions thereof or mixtures of any of the foregoing, for the treatment of autoimmune diseases in general or those mentioned above, in particular, is also encompassed by the present invention.

DESCRIPTION OF THE FIGURES

FIGS. 1A–B show PPD-induced protection against EAE. (A) Mice pre-immunized with PPD are resistant to induction of EAE. SJL/J mice were injected with 50 μg of PPD in IFA 21 to 25 days before the encephalitogenic challenge as described in Materials and Methods. X denotes mortality in all mice in the group. (a) and (b) correspond to p values of 0.0003 and 0.0001, respectively, when compared with paralysis (P) or mortality (M) in the combined control groups (none+IFA). (B) Silver-stained SDS-gel of the PPD preparation used throughout in the present application. Twenty μg PPD were run on the gel. Molecular weights of standards (Bio-Rad, Richmond, Calif.) are shown on the right of the gel.

FIGS. 2A–B show RPLC fractionation of PPD. (A) Chromatographic profile. Two mg PPD were injected per RPLC run and eluted with a 0 to 50% linear gradient of 1-propanol in 0.1% trifluoroacetic acid (TFA). Pooled fractions are indicated by Roman numerals. (B) Silver-stained SDS-gel of pooled fractions II through VIII. Four μg of pooled fraction were loaded per lane.

FIGS. 4A–C show further purification of the PPD component responsible for imparting protection against EAE. (A) RPLC refractionation of PPD fraction V, highly protective against EAE: chromatographic profile. Fraction V (150 μg) derived from RPLC fractionation of 12 mg PPD (6 chromatographic runs) was refractionated by RPLC which was developed with a 0 to 60% linear gradient of 1-propanol. Resulting fractions were pooled as indicated and are represented by capital letters. (B) Silver-stained SDS-gel of Fr D, protective against EAE. Four μg of protein were loaded on the gel. (C) Analysis of the protective effect against EAE by the major pooled fractions of rechromatographed PPD fraction V. Major pooled fractions (Fr-B, D and F) obtained from rechromatography of PPD fraction V were injected s.c. (1.5 μg protein in IFA) 24 days prior to encephalitogenic challenge. X denotes mortality in all mice in the group. (a) and (b) correspond to p values of 0.0005 and 0.0001, respectively, when compared with P in combined control groups (none+IFA), (c) to p=0.0001 when compared with M in combined control groups (none+IFA). Fractions B, D and F were also tested in vitro for their ability to stimulate EAE-mediating T lymphocytes specific for MBP 89–101 (DSBP line cells) or PLP 139–151 (NSPLP line cells) or T lymphocytes specific for PPD (DSP line cells). The results (summarized in A below the graph) showed that none of the fractions had a stimulatory effect on EAE-mediating T lymphocytes. Only the fraction which induced protection against EAE (Fraction D) stimulated PPD-specific cells (DSP line cells).

FIGS. 5A–C show the protective activity of the 12-kDa PPD protein purified by preparative gel electrophoresis (A) Silver-stained SDS-gel of Fraction D and the 12-kDa protein eluted from the gel. The 12-kDa eluted protein also stimulates PPD-reactive T lymphocytes, but not MBP- or PLP-specific T cells. Fraction D was electrophoresed on two preparative gels and the gel band corresponding to the 12-kDa protein was sliced out and the protein was eluted out of the gels as described in Materials and Methods. Lane 1 shows the electrophoretic separation of Fraction D components (4 μg/lane) and lane 2 shows the 12-kDa protein (approx. 1 μg/lane) of Fraction D eluted from the gel. As indicated below the respective lanes, Fraction D and its 12-kDa component were identical in their ability to induce the proliferation of T lymphocytes specific for PPD (DSP line cells), but had no effect on EAE-mediating T lymphocytes specific for MBP 89–101 (DSBP line cells) or PLP 139–151 (NSPLP line cells). (B) Two-dimensional gel electrophoretic analysis of gel-eluted 12-kDa protein of Fraction D. Approximately 3–4 μg were run on the first-dimension gel. The silver-stained second-dimension gel is shown. The gel-eluted 12-kDa protein appears as several contiguous spots, most likely representing post-translationally modified isoforms. (C) Protective effect of the gel-eluted 12-kDa protein of Fraction D. SJL/J mice were injected with 1.5 μg of the gel-eluted 12-kDa protein or of Fraction D emulsified in IFA 22 days prior to the encephalitogenic challenge. X denotes mortality in all mice in the group. (a), (b) and (c) correspond to p values of 0.04, 0.001 and 0.007, respectively, when compared with P in combined control groups (none+IFA); (d) to p=0.001 when compared with M in combined control groups (none+IFA).

DETAILED DESCRIPTION OF THE INVENTION

In accordance with the present invention, the protective activity of Mt against induction of EAE in SJL/J mice is attributed to a protein of approximately 12-kDa in size purified from PPD. Sequencing of the first 17 N-terminal amino acids of this 12-kDa PPD protein seemed to indicate that it was identical, or closely related, to the 10-kDa BCG-a antigen of Mt. However, differences in protective activity and T-cell epitope specificity between the two proteins appear to refute this possibility. Thus, in contrast to the 12-kDa PPD protein, the 10-kDa BCG-a protein did not protect against EAE and did not stimulate PPD-specific T lymphocytes. Reciprocal analysis of the proliferative response to the 12-kDa PPD protein by 10-kDa BCG-a protein-reactive T cells demonstrated low cross-reactivity, supporting the notion that the two proteins share sequence homology but are not identical.

The above noted biologic characteristics of the 12-kDa PPD protein of the invention opens the way for using this 12-kDa PPD protein in the treatment of human autoimmune diseases. It is stimulatory for PPD-specific T lymphocytes, but appears to do so without stimulation of other potentially pathogenic T lymphocytes, indicating that this 12-kDa PPD protein may be used as a potentially safe therapeutic agent for human autoimmune diseases.

As mentioned above, EAE is the well-established and widely accepted animal model for ascertaining the effects of agents which may be involved in human autoimmune diseases. The isolation and purification in accordance with the present invention of the 12-kDa PPD protein that affords protection against EAE in mice, is thus indicative that this protein is useful in the treatment of autoimmune diseases in human, in general, and, in particular, diseases such as multiple sclerosis, rheumatoid arthritis, systemic lupus erythematosus, insulin-dependent diabetes mellitus and graft-versus-host disease.

Therefore, the present invention concerns the 12-kDa PPD protein characterized by its ability to elicit protection against EAE and to stimulate PPD-specific T lymphocytes, being thus useful for the treatment of autoimmune diseases, and comprising the following 17 amino acid N-terminal sequence : Ala-Lys-Val-Asn-Ile-Lys-Pro-Leu-Glu-Asp-Lys-Ile-Leu-Val-Gln-Ala-Asn. (residues 2–18 of SEQ ID NO:1). Also encompassed by the present invention are salts, functional derivatives and analogs of the 12-kDa PPD protein and active fractions thereof, which are also characterized by having the ability to elicit protection against EAE and to stimulate PPD-specific T lymphocytes.

The native 12-kDa PPD protein of the invention may be obtained from the PPD of Mt by any standard purification procedure, including affinity chromatography using antibodies specific for the protein.

In one preferred embodiment, the process for producing the substantially purified 12-kDa PPD protein comprises: (a) fractionating PPD derived from *Mycobacterium tuberculosis* (Mt) by RPLC; (b) selecting and isolating the biologically active fractions from (a) that provide highest protection of mice against EAE; (c) subjecting said 12-kDa PPD protein from the isolated fractions of (b) to RPLC and isolating the fractions having the highest protection against EAE; and (d) purifying the 12-kDa PPD protein from the isolated fractions of (c) by preparative gel electrophoresis.

Alternatively, the 12-kDa PPD protein may be produced as a recombinant protein using standard recombinant DNA methods, and hence the present invention also encompasses all of the tools used in these procedures, i.e. the DNA molecules comprising the nucleotide sequence coding for the 12-kDa PPD protein or for a protein substantially homologous therewith, suitable recombinant expression vectors containing the DNA molecules, and suitable (eukaryotic or prokaryotic) host cells transformed by the expression vectors and capable of expressing the protein.

As used herein "salts" refers to both salts of carboxyl groups and to acid addition salts of amino groups of the protein molecule formed by means known in the art. Salts of carboxyl group include inorganic salts, for example, sodium, calcium, and salts with organic bases as those formed, for example, with amines, such as triethanolamine, arginine or lysine. Acid addition salts include, for example, salts with mineral acids and salts with organic acids.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e. they do not destroy the activity of the protein and do not confer toxic properties on compositions containing it. These derivatives include aliphatic esters or amides of the carboxyl groups, N-acyl derivatives of free amino groups or O-acyl derivatives of free hydroxyl groups formed with acyl moieties (e.g. alkanoyl or carbocyclic aroyl groups) and derivatives with sugar or phosphate residues, e.g., those formed by post-translational modification.

"Analogs" are proteins having the activity of the 12-kDa PPD protein of the invention, but that represent modifications of the protein including deletions, substitutions or additions of one or more amino acid residues of the native 12-kDa PPD amino acid sequence; all such modifications being effected either by known chemical procedures (in the case of deletions and additions) or by standard recombinant DNA methods (in all cases). Suitable modifications, i.e. analogs are only those which retain the biological activity of the 12-kDa PPD protein.

As "active fractions" of the substantially purified protein, the present invention covers any fragment or precursors of the polypeptide chain of the protein molecule alone or together with associated molecules or residues linked thereto. e.g. sugar or phosphate residues, or aggregates of the protein molecule or the sugar residues by themselves, provided said fraction has the biological activity of the 12-kDa PPD protein.

The present invention also concerns pharmaceutical compositions comprising a pharmaceutically active carrier and the 12-kDa PPD protein, a salt, analog, functional derivative or an active fraction thereof. These compositions mat be used to elicit protection against autoimmune diseases, in general, and diseases such as multiple sclerosis, rheumatoid arthritis, systemic lupus erythematosus, insulin-dependent diabetes mellitus and graft-versus-host disease, in particular.

The way of administration can be via any of the accepted modes of administration for similar agents and will depend on the condition to be treated, e.g. intravenously, intramuscularly, subcutaneously, by local injection, by topical application or per os, as the case may require.

The pharmaceutical compositions of the invention are prepared for administration by mixing the protein, a salt, analog, functional derivative or active fraction thereof with physiologically acceptable carriers, stabilizers and excipients, and prepared in dosage form, e.g. by lyophilization in dosage vials. The amount of active compound to be administrated will depend on the route of administration, the disease to be treated and the condition of the patient. Local injection, for instance, will require a lower amount on a body weight basis than will e.g. intravenous injection.

The invention also encompasses a method for treatment of a patient afflicted with an autoimmune disease (i.e. multiple sclerosis, rheumatoid arthritis, systemic lupus erythematosus, insulin-dependent diabetes mellitus and graft-versus-host disease) which comprises administering to said patient an effective amount of a 12-kDa PPD protein, a salt, functional derivative, analog or active fraction thereof or a mixture of any of the foregoing.

The present invention will now be described in more detail in the following non-limiting Examples and the accompanying figures:

EXAMPLES

Materials and Methods a) Mice. Female SJL/J mice were purchased from Jackson Laboratories (Bar Harbor, Me.). All mice were 2–3 months old when used in the experiments.

b) Antigens and T-cell lines. PPD was purchased from Statens Serum Institute (Copenhagen, Denmark). Recombinant 10-kDa BCG-a protein, batch MT10-1A, produced and purified by Dr. V. Mehra (see Mehra et al., 1992), and 65-kDa M. bovis protein were donated by Dr. J. van Embden of the National Institute of Public Health and Environmental Protection, Bilthoven, the Netherlands. Peptides corresponding to amino acid residues 89–101 of MBP (MBP 89–101) and to amino acid residues 139–151 of proteolipid protein (PLP 139–151) were synthesized by the Weizmann Institute Synthesis Unit, using a solid phase technique on a peptide synthesizer (Applied Biosystems Inc., Foster City, Calif.). T-cell lines, encephalitogenic for SJL/J mice and specific for the 89–101 epitope of MBP or for the 139–151 epitope of PLP, were selected in vitro as previously described (Ben-Nun and Lando, 1983; Ben-Nun and Cohen, 1982), from SJL/J mice immunized with MBP 89–101 or PLP 139–151 peptides respectively. T-cell line specific for PPD was selected in vitro from SJL/J mice immunized with complete Freund's adjuvant (CFA). All T-cell lines were maintained in vitro in medium containing IL-2 with alternate stimulation in vitro with the relevant antigen, every 10–14 days as previously described (Ben-Nun and Cohen, 1982).

c) Fractionation of PPD by reverse phase liquid chromatography. Fractionation of PPD was achieved by reverse phase liquid chromatography (RPLC) run on a wide-bore column (Aquapore RP-300, 7 μm, 200×6×4 mm), using a linear gradient of 1-propanol (0 to 50%) in 0.1% trifluoroacetic acid, with a flow rate of 0.75 or 1.0 ml/min (run time 50 min). Two mg of PPD were injected per run and the protein separation was performed with a Spectra Physics SP8750 HPLC system and a Waters Model 441 detector at 214 nm. Pooled fractions were freeze-dried and reconstituted in double-distilled $H_2O$. Protein concentrations were measured using the Bio-Rad Protein Assay kit (Bio-Rad, Richmond, Calif.).

d) SDS-PAGE, electroblotting and N-terminal amino acid microsequencing. Polyacrylamide gel electrophoresis in the presence of sodium dodecyl sulphate (SDS-PAGE) was carried out on 15% slab gels according to the method of Laemmli (Laemmli, 1970). The resulting electrophoretograms were blotted onto polyvinylidene difluoride membrane (PVDF) according to the method of Towbin (Towbin et al., 1979), and relevant protein bands were cut out of the membrane and sequenced directly according to the procedure of Matsudaira (Matsudaira, 1987), using an Applied Biosystems Model 475A sequenator.

e) Elution of PPD protein from SDS-gels. PPD-derived fractions were electrophoresed on preparative SDS-gels, and the relevant PPD proteins, located by staining of side lanes, were eluted from the cut-out gel bands by passive diffusion. The resulting preparations were dialyzed extensively against double-distilled $H_2O$, lyophilized and resuspended in PBS.

f) Two-dimensional gel electrophoresis. Two-dimensional (2-D) gel electrophoresis of the 12-kDa PPD protein eluted from the gel band was performed according to the method of O'Farrell (O'Farrell, 1975), using Ampholine pH 3.5–10.0 from Sigma Chemical Co. (Cat. no. A-5174; St Louis, Mo.). The second-dimension electrophoresis was run on 15% gels and silver-stained.

g) T-cell proliferative responses. SJL/J T line cells ($1.5 \times 10^4$) specific for MBP 89–101 (DSBP line), PLP 139–151 (NSPLP line), or PPD (DSP line) were cultured in microtiter wells in the presence of irradiated (2500 rads) syngeneic spleen cells, as accessory cells, in 0.2 ml RPMI medium supplemented with L-glutamine, β-mercaptoethanol, antibiotics and 2.5% fetal calf serum as previously described (Ben-Nun and Lando, 1983). Popliteal lymph node cells ($5 \times 10^5$) isolated from SJL/J mice, injected s.c. in the hind footpads with 2.5 μg recombinant 10-kDa BCG-a protein in IFA, were cultured in microtiter wells in 0.2 ml RPMI medium supplemented with L-glutamine, β-mercaptoethanol, antibiotics and 0.5% syngeneic serum as previously described (Ben-Nun and Lando, 1983). The relevant antigen (MBP 89–101, PLP 139–151, PPD or PPD-derived fraction or gel-eluted protein, or recombinant 10-kDa BCG-a protein) was added (2 μg/well for MBP and PLP peptides or PPD; 0.5 μg/well and 1.5 μg/well for PPD-derived fraction and gel-eluted protein, or recombinant 10-kDa BCG-a protein) in triplicate cultures. The cultures were incubated for 48 hrs at 37° C. in humidified air containing 7.5% $CO_2$. [$^3$H]-thymidine (1 μCi/well) was added for the last 16 hrs of the incubation and the cultures were then harvested and counted using a Matrix 96 Direct beta counter (Packard Instr., Meriden, Conn.). The proliferative response is measured as the [$^3$H]-thymidine incorporation expressed as mean counts per minute (cpm) of triplicate cultures.

h) Induction of EAE and protection against the disease. EAE was induced in mice as previously described (Ben-Nun and Lando, 1983; Ben Nun et al., 1993). Briefly, 0.1 ml of emulsion prepared from mouse spinal cord homogenate (MSCH, 60 mg/ml) emulsified with an equal volume of CFA enriched for M. tuberculosis H37Ra (5 mg/ml) was injected s.c. into the mouse footpads. Immediately after and 48 hrs later, pertussigen was injected intravenously (400 ng/mouse;

pertussigen was a kind gift from Dr. D. Teitelbaum of the Weizmann Institute). For the induction of protection against the disease, mice were injected s.c. in the flanks with 0.1 ml of PBS/IFA emulsion containing 50 μg PPD, 1.5 μg PPD-derived fractions, gel-eluted PPD protein, or 2.5 μg of recombinant 10-kDa BCG-a protein, 21 to 25 days before the encephalitogenic challenge.

i) Clinical evaluation, scoring and statistical analysis. Following the encephalitogenic challenge, mice were observed daily for clinical signs of EAE. The severity of the clinical manifestations was scored daily for each individual mouse in the treatment group on a scale of 0 to 6; 0: no clinical signs, 1: loss of tail tonicity, 2: flaccid tail, 3: hind leg paralysis, 4: hind leg paralysis with hind body paresis, 5: hind and fore leg paralysis, 6: death. Results presented denote the mean score of the treatment group on each given day after encephalitogenic challenge. At the peak of the clinical disease, on days 12 to 17 after encephalitogenic challenge, the standard errors (not shown) were less than 16% of the mean clinical score. Each graph (see FIGS. 1A, 3A, 4C, 5C and 7A) also displays the incidence of paralysis (P) and mortality (M) for each treatment group in order to allow a complete evaluation of the clinical course of EAE.

To evaluate the statistical significance of the differences in incidence of paralysis or mortality between treatment and control groups in each experiment, the contingency table analysis was used to calculate the $\chi^2$ values with the Stat View 512+ program. Due to the relatively small number of mice in each group, the p values given are of $\chi^2$ with continuity correction.

Example 1

Figure 1A:
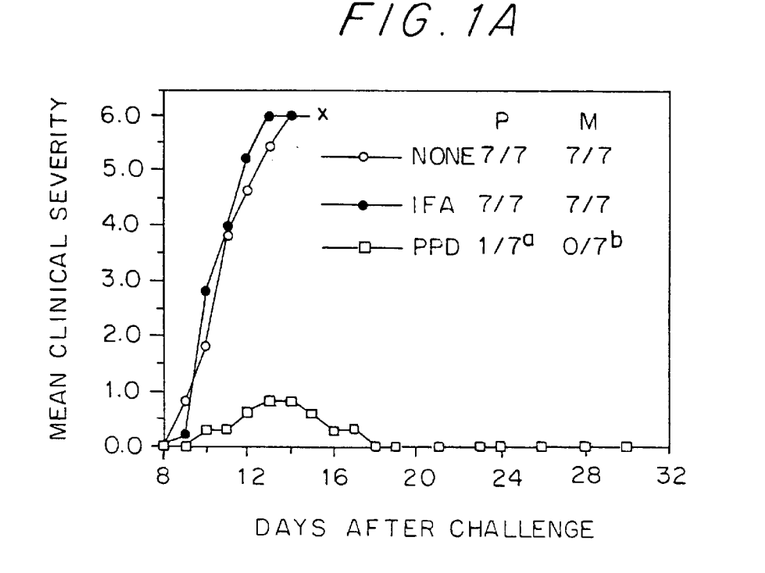
Figure 1B:
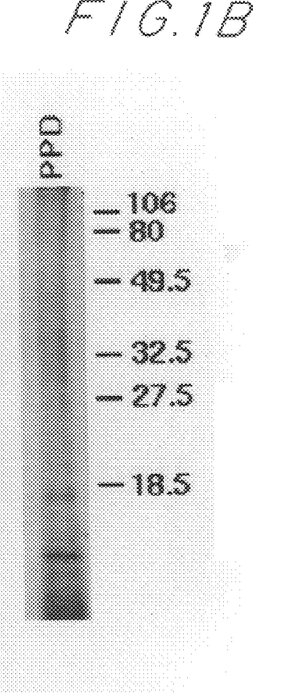
Figure 2A:
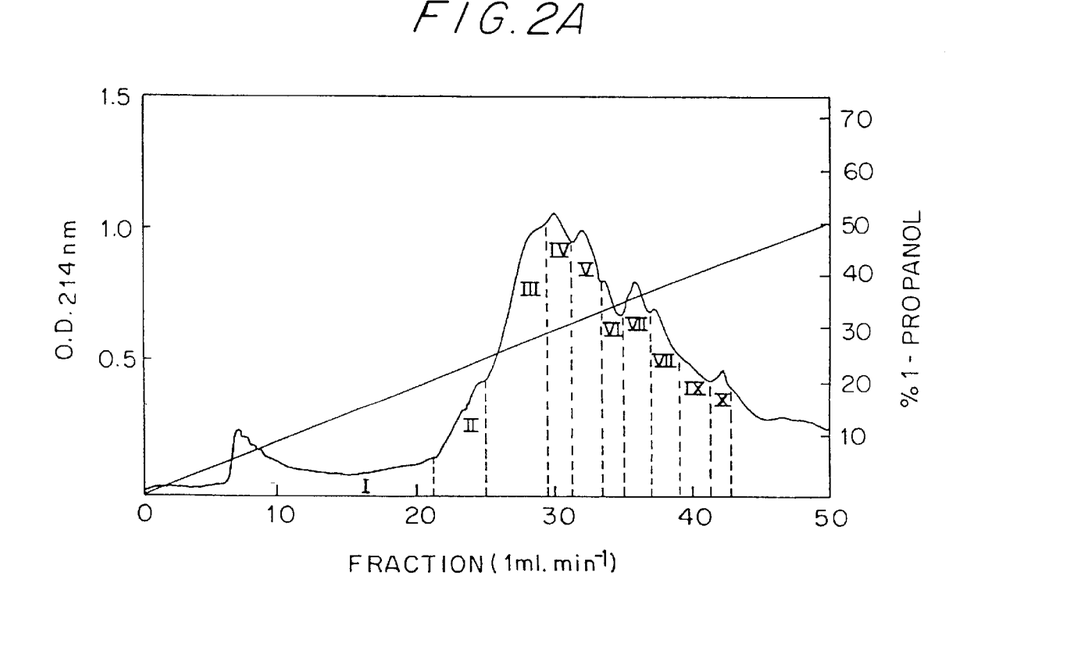
Figure 2B:
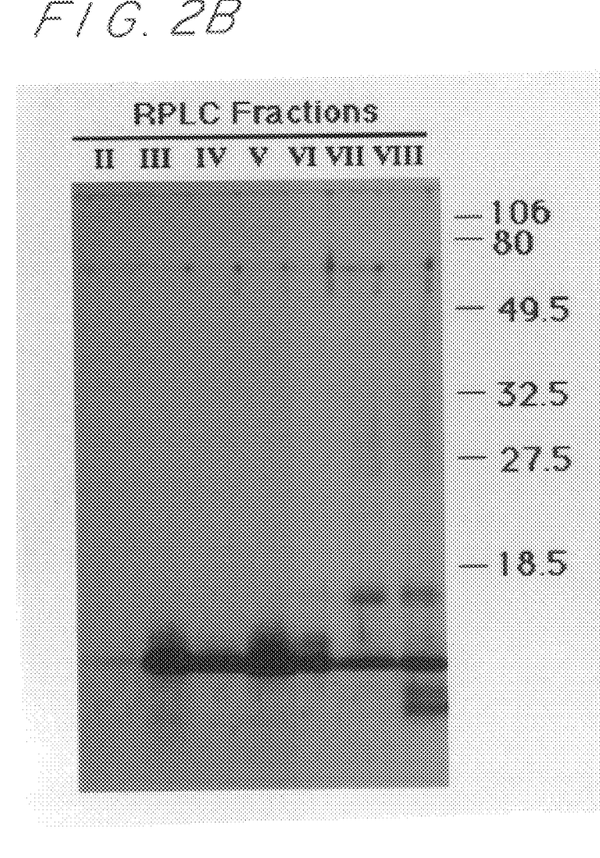
Figure 3A:
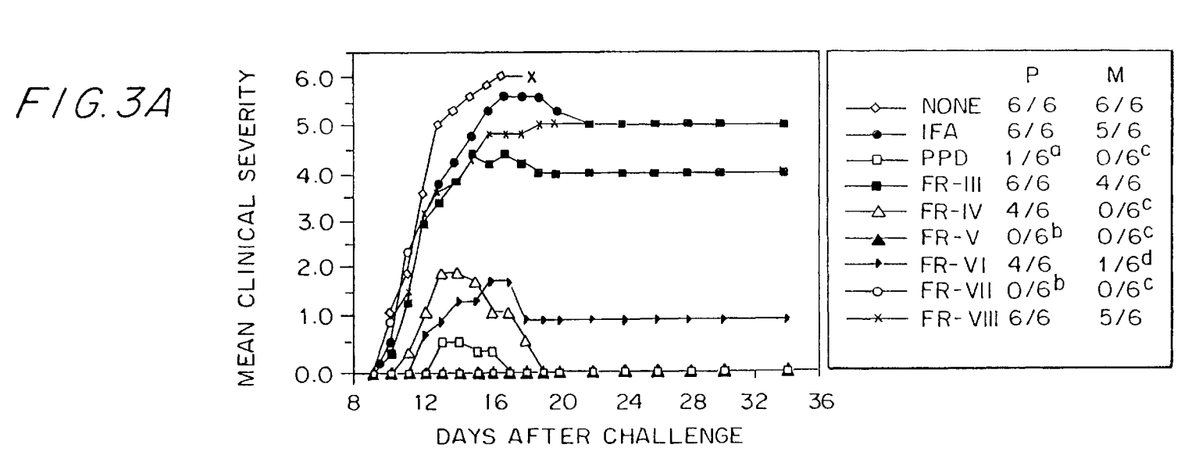
FIGS. 3A–B show that protection against EAE by PPD fractions is not associated with a stimulatory effect on EAE-mediating T-cells, but correlates with their ability to stimulate PPD-specific T lymphocytes. (A) Protective effect of PPD fractions. SJL/J mice were injected with 1.5 μg of the indicated PPD fractions emulsified in IFA 22 days prior to the encephalitogenic challenge. X denotes mortality in all mice in the group. (a) and (b) correspond to p values of 0.0016 and 0.0002, respectively, when compared with P in combined control groups (none+IFA); (c) to p=0.0012 and (d) to p=0.004 when compared with M in combined control groups (none+IFA). (B) Effect of PPD fractions on T-cell lines specific for MBP 89–101 (DSBP cells) or PPD (DSP cells). The proliferative response to the indicated PPD fractions (0.5 μg/well) was measured as detailed in Materials and Methods. Vertical bars represent standard deviation from the mean of triplicate cultures. It should be noted that none of the PPD fractions were stimulatory for PLP-specific T cells (data not shown).

RPLC Fractionation of PPD Yields Discrete Fractions with Protective Activity FIG. 1A shows protection against the induction of EAE in SJL/J mice pre-treated with the PPD preparation used throughout the examples in the present application. The extent of protection was comparable to that previously observed (Ben-Nun et al., 1993). SDS-PAGE analysis (FIG. 1B) of this PPD preparation shows the presence of proteins of different sizes, with a band of an approximate molecular weight of 12-kDa being the most abundant. To identify which of these proteins protect against EAE, PPD was fractionated by RPLC (FIG. 2A). Analysis of the resulting fractions revealed the presence of a 12-kDa protein(s), most predominantly in fractions III–VIII (FIG. 2B). These fractions were tested in vivo for their protective activity (FIG. 3A). Mice were injected s.c. with an equivalent of 1.5 μg PPD fraction emulsified in IFA, three weeks prior to the encephalitogenic challenge, and the effect of the various fractions on the development of EAE was followed. Daily clinical scoring for EAE of mice pre-treated with some of the fractions (fractions III–VIII) is shown in FIG. 3A. In contrast to control mice, untreated or treated with IFA alone, which developed severe paralysis with a high mortality rate, mice pre-treated with fractions V and VII were fully protected. Other fractions either had no protective effect or induced only partial protection against the induction of EAE (FIG. 3A). The partial protective effect of fractions IV and VI could be attributed to contamination of these fractions with fraction V, due to tailing of the fraction V peak.

Example 2

Figure 3B:
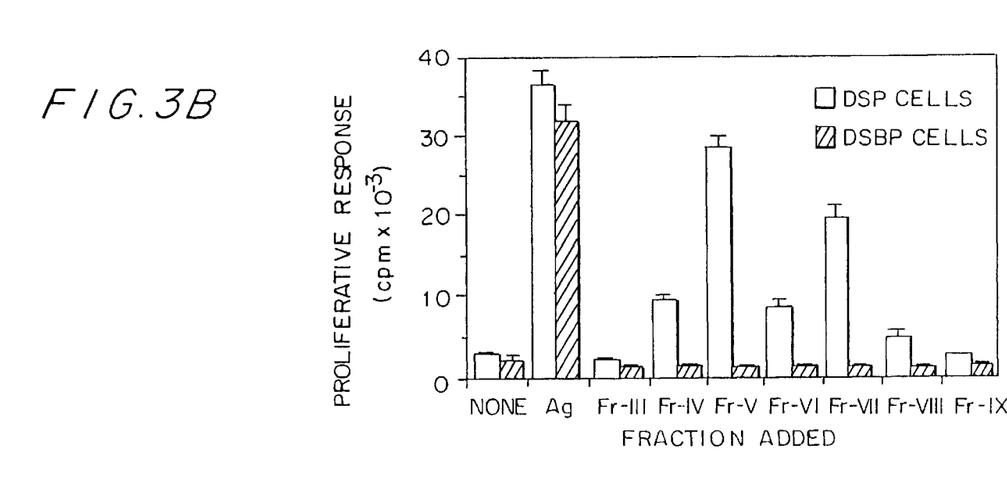

RPLC Fractions Which Protect Against EAE Stimulate PPD Cells, but Not Encephalitogenic T Cells To investigate the possibility that the protection by PPD fractions was mediated via shared T cell epitopes between the major encephalitogenic protein and a component of the protective PPD fraction, PPD fractions were assayed for their ability to stimulate encephalitogenic T lymphocytes in vitro. None of the fractions, including those which were highly protective against EAE, were stimulatory for T-lymphocytes specific for MBP (FIG. 3B) or PLP (data not shown). Paradoxically, a correlation was observed between the protective effect of the fractions and their ability to stimulate PPD-specific T lymphocytes. Thus, fractions V and VII which conferred a complete protection against EAE also stimulated the PPD-specific T cells to the highest degree (FIG. 3, A and B).

Example 3

Figure 4A:
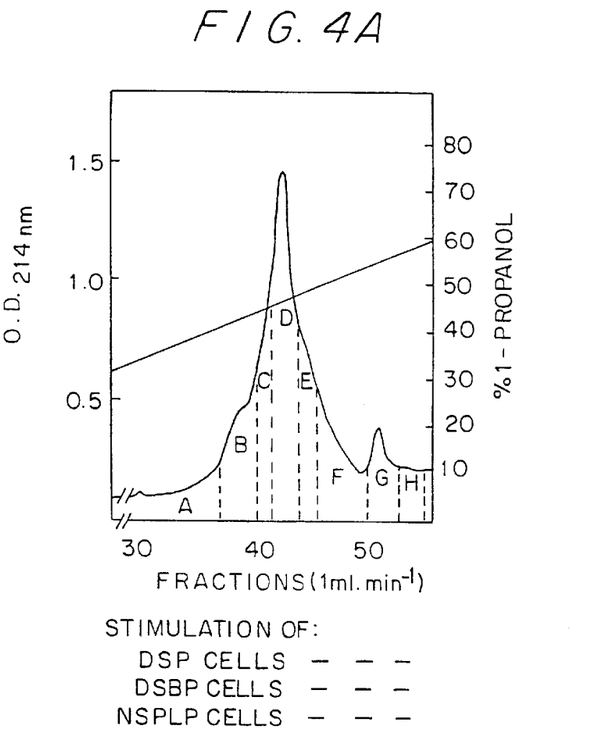
Figure 4B:
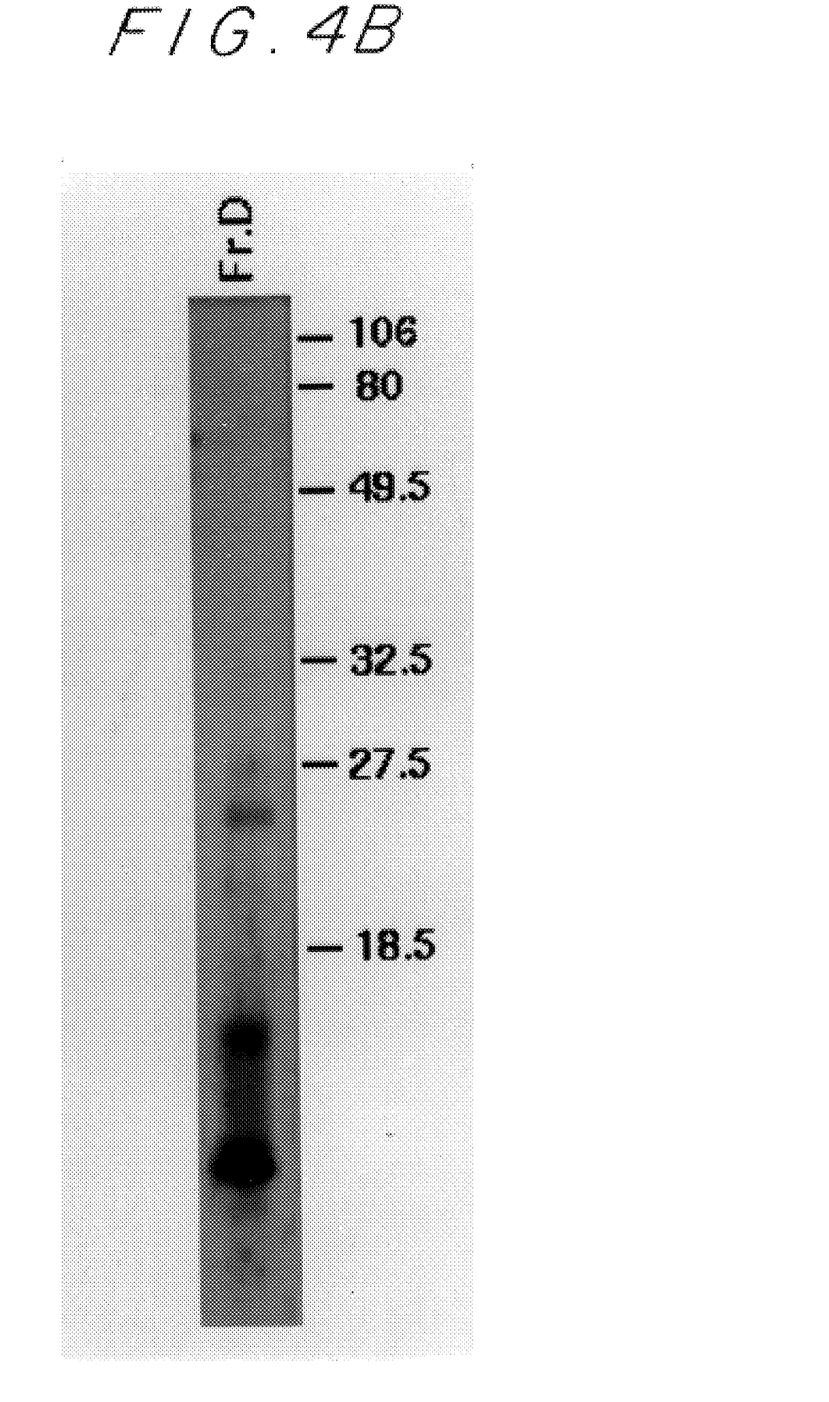
Figure 4C:
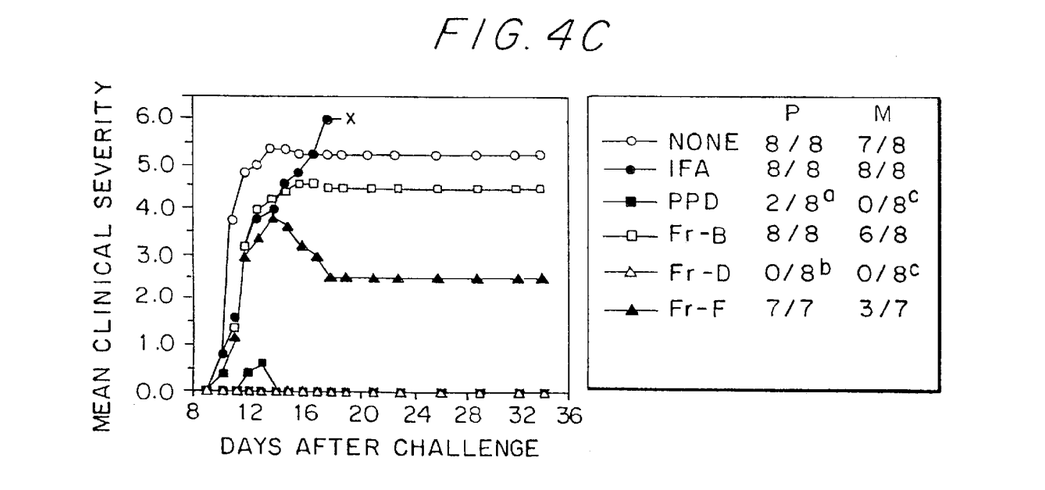

A 12-kDa Protein Purified by RPLC Refractionation and Preparative Gel Electrophoresis Imparts Protection Against EAE From the results shown above, the protective activity could not be readily assigned to the most abundant protein, which migrates on SDS-PAGE with a molecular weight of 12-kDa, in the PPD fractions that protected against EAE. Thus, 12-kDa proteins were also observed to be predominant in PPD fractions that had no effect on the development of EAE, such as fractions III and VIII (FIGS. 2 and 3). Furthermore, fraction VII, one of the two fractions that were highly protective against EAE, contained protein(s) other than the 12-kDa protein (FIG. 2). In the attempt to identify a component which is capable of conferring complete protection against the disease, fraction V, which showed the highest protective activity, was further investigated. RPLC refractionation of this PPD fraction yielded a major peak, Fr. D, that eluted at about 45% 1-propanol (FIG. 4A). This peak was highly protective against EAE (FIG. 4C) and also had the ability to stimulate PPD-specific T-cells, but not MBP- or PLP-specific encephalitogenic T lymphocytes (FIG. 4A). SDS-PAGE analysis of Fr. D revealed a major protein of 12-kDa in size (FIG. 4B). Unexpectedly, two proteins of approximate molecular weight 16 kDa and 26 kDa were also detected (FIG. 4B). It is unclear whether these bands are a result of the enrichment of other proteins upon further purification, or whether they represent dimerization of the 12-kDa protein and/or aggregation of the 12-kDa protein with peptide fragments contained in the preparation.

Figure 5A:
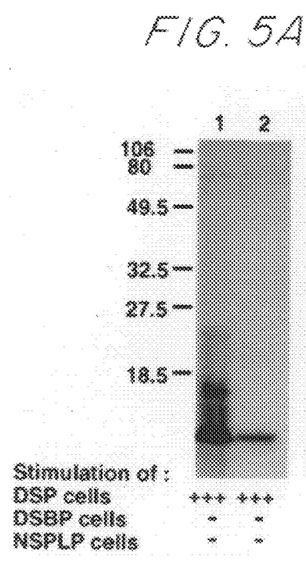

To determine conclusively the protective role of the 12 k-Da protein, Fr. D was electrophoresed on SDS-polyacrylamide gel; the 12-kDa protein-containing band was sliced out and the protein was eluted. It migrated as a single, 12-kDa band on one-dimensional SDS-PAGE (FIG. 5A), was as highly protective against the induction of EAE as Fr. D (FIG. 5C) and strongly stimulated PPD-specific T cells, but could not induce a proliferative response by the encephalitogenic MBP- or PLP-specific T cells (FIG. 5A).

Figure 5B:
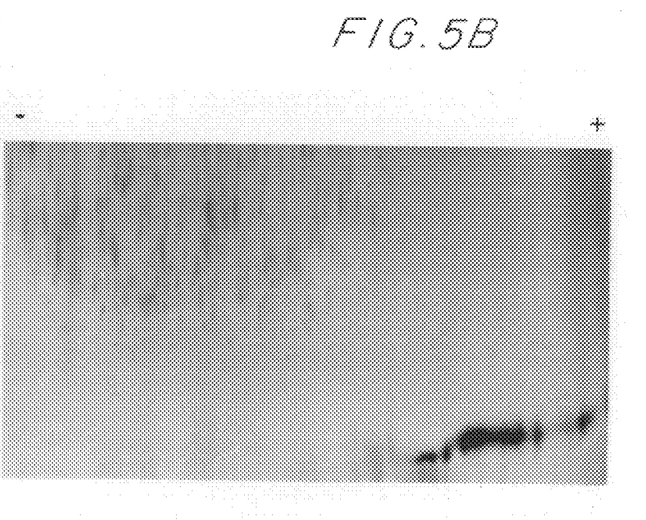
Figure 5C:
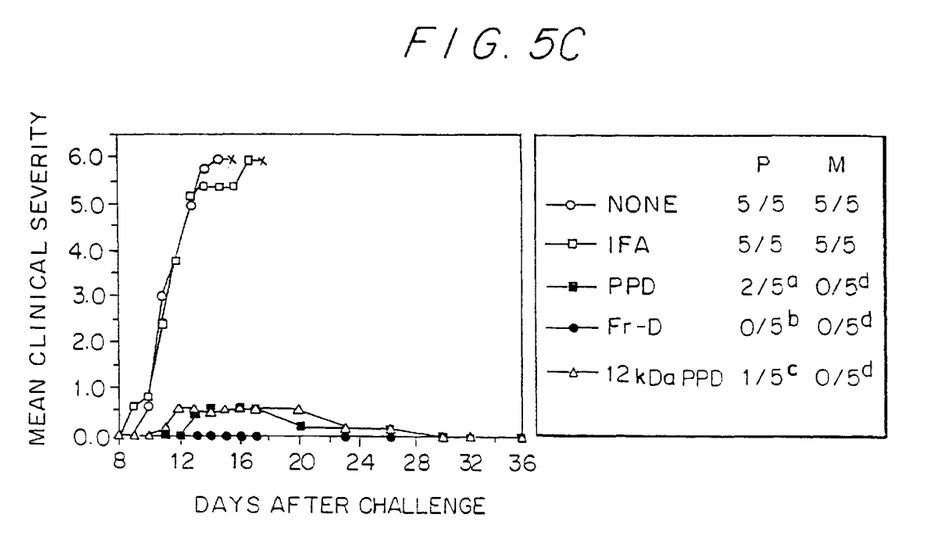

Two-dimensional gel analysis of the gel-eluted 12-kDa protein resulted in an electrophoretic pattern more consistent with post-translationally modified isoforms of a single protein than with a mixture of proteins (FIG. 5B), although the spread-out pattern of the charge isoforms makes it difficult to absolutely exclude the possibility that another protein is present in the gel-eluted band. The likelihood that the two-dimensional gel pattern is caused by charge isoforms rather than by the presence of a mixture of proteins would be strengthened if an unambiguous N-terminal amino acid sequence could be obtained from the gel-eluted protein.

Example 4

Figure 6:
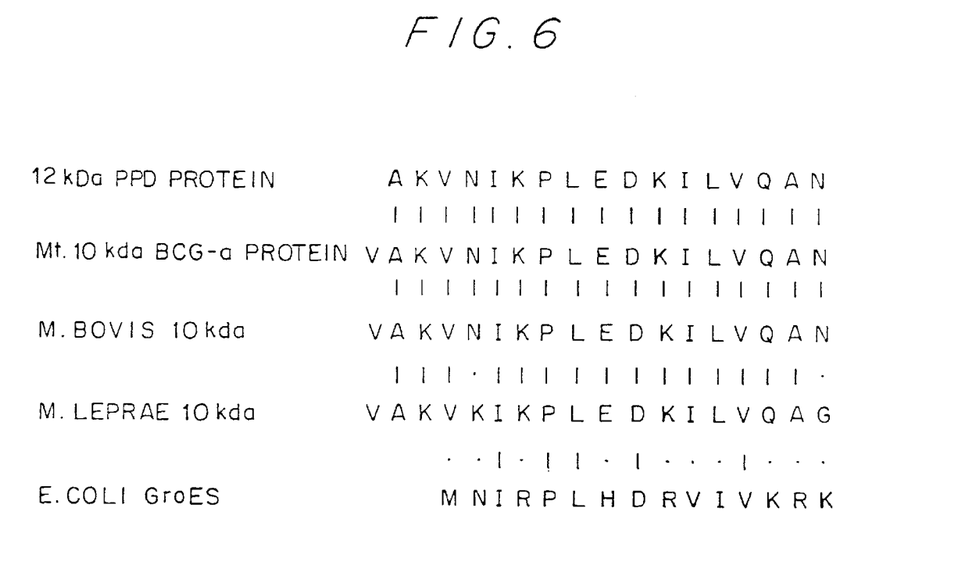
FIG. 6 shows that the N-terminal amino acid sequence of the 12-kDa protein purified from PPD (residues 2–18 of SEQ ID NO:1) is identical to that of the 10-kDa protein of Mt./M. bovis (SEQ ID NO:1). The 12-kDa protein of Fraction D was transferred onto PVDF membrane either by electroblotting of the electrophoretogram or by elution from the gel band and spotting. The protein adsorbed to the membrane was then subjected to amino acid microsequencing. Sequences of the 10-kDa protein of M. tuberculosis (SEQ ID NO:1), M. bovis (SEQ ID NO:1)and M. leprae (SEQ ID NO:2) were from Shinnick et al. 1989, Yamaguchi et al. 1988 and Mehra et al. 1992, respectively. The sequence of E. coli GroES (SEQ ID NO:3) was from Shinnick et al. 1989.

The Protective 12-kDa PPD Protein Shares Identical N-terminal Sequence with BCG-a Protein To gain some knowledge on the nature of the protective protein, Fr. D was electrophoresed and blotted onto PVDF-membrane and the 12-kDa protein band was cut out and subjected to N-terminal amino acid microsequencing. As shown in FIG. 6, the 17 N-terminal amino acids of the 12-kDa PPD protein were identified and found to be homologous to the 17 N-terminal amino acids of the 10-kDa BCG-a protein of *M. tuberculosis.*

Example 5

Figure 7A:
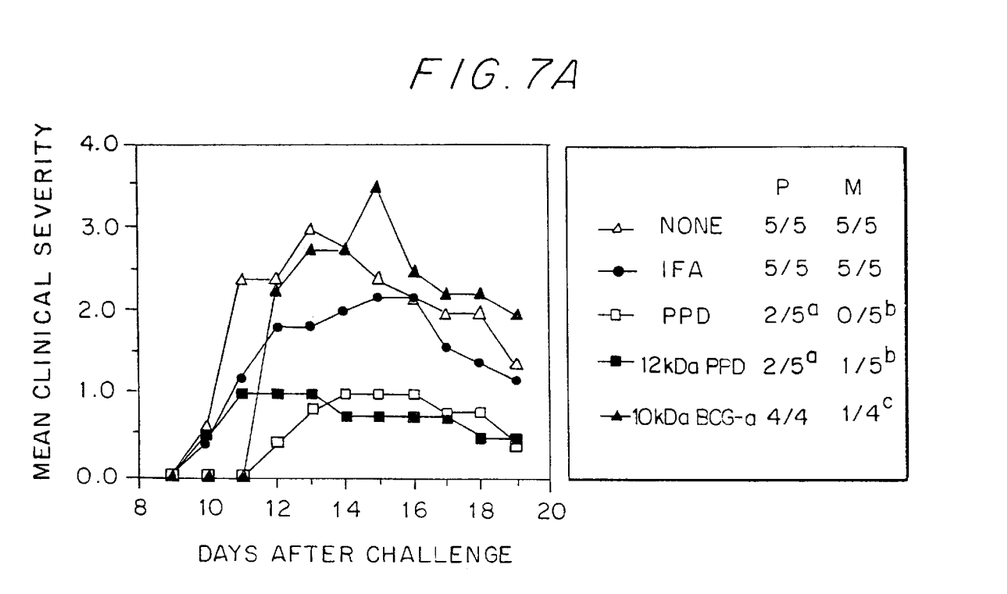
FIGS. 7A–B show that recombinant 10-kDa BCG-a protein does not protect against EAE and does not stimulate PPD line T cells. (A) Mice pre-immunized with recombinant 10-kDa BCG-a protein are not protected against EAE. SJL/J mice were injected with recombinant 10-kDa BCG-a protein (2.5 μg), 12-kDa PPD protein (1.5 μg) or PPD (50 μg) emulsified in IFA, 21 days before the encephalitogenic challenge. (a) corresponds to p=0.032 when compared with P in combined control groups (none+IFA); (b) to p=0.0001 and (c) to p=0.0003 when compared with M in combined control groups (none+IFA). (B) Recombinant 10-kDa BCG-a protein does not induce proliferation of PPD-specific T line cells. The proliferative response by PPD-specific T line cells to PPD (4 μg), recombinant 10-kDa BCG-a protein (0.5 μg) and 12-kDa PPD protein (0.5 μg) was measured as detailed in Materials and Methods. Vertical bars represent standard deviation from the mean of triplicate cultures. Higher concentrations of recombinant 10-kDa BCG-a protein did not induce increased responses by the PPD-specific T cells (data not shown).
Figure 7B:
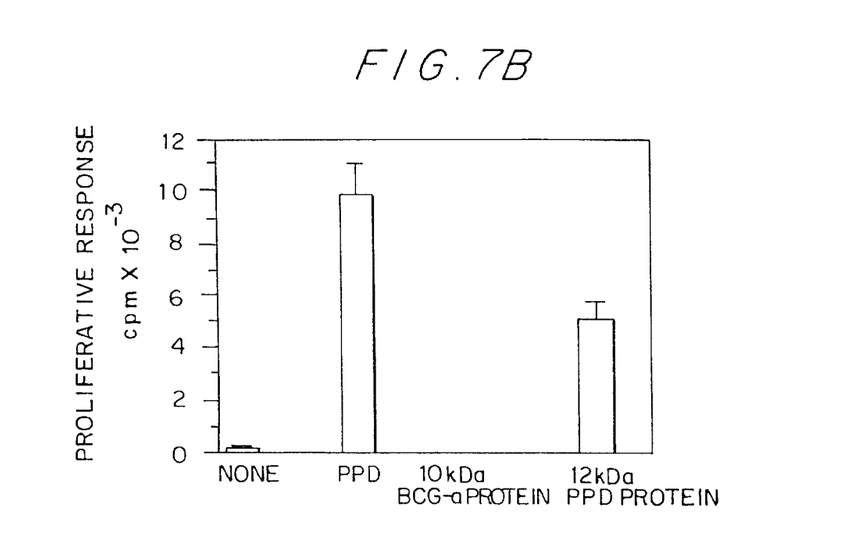

The 10-kDa BCG-a Protein and the 12-kDa PPD Protein Differ in Their Ability to Protect Against EAE To investigate the possibility that the 12-kDa PPD protein is identical to the 10-kDa BCG-a protein, as suggested by the N-terminal sequence data, the purified 12-kDa PPD protein and recombinant 10-kDa BCG-a protein were compared for their ability to protect against EAE. In contrast to the 12-kDa PPD protein, the 10-kDa BCG-a protein was found to be ineffective in imparting protection against EAE (FIG. 7A). These two proteins were also compared for their ability to induce proliferative responses by PPD-specific T cells in vitro. As shown in FIG. 7B, no stimulation of PPD-specific T cells by the 10-kDa BCG-a protein was observed, whereas the cells responded well to the 12-kDa PPD protein, indicating that the 12-kDa PPD protein and the 10-kDa BCG-a protein do not share the epitope(s) recognized by the PPD-specific T line cells. Confirmation that the two proteins are not identical was obtained by assessing the antigenic specificity of lymph node cells isolated from mice primed with 10-kDa BCG-a protein in IFA. As shown in Table I, the primed cells responded poorly to the 12-kDa PPD protein and moderately to PPD, as compared with their response to the immunising 10-kDa BCG-a protein. Altogether, these data demonstrate that the two proteins share sequence homology but are not identical, and suggest that the T cell epitopes of the protective 12-kDa PPD protein, which are different from those of the 10-kDa BCG-a protein, are likely to be implicated in the overall protective process.

TABLE 1

Reactivity of lymph node cells (LNC) isolated from mice immunized with 10-kDa BCG-a protein

| Antigen | Proliferative response of primed LNC Mean cpm ± SD (SI) | |
|---|---|---|
| | Expt. 1 | Expt. 2 |
| None | 624 ± 56 | 1472 ± 100 |
| 10 kDa BCG-a protein | 11464 ± 2444(18.3) | 15325 ± 1294(10.4) |
| 12 kDa PPD protein | 1442 ± 65(2.3) | 6005 ± 466(4.0) |
| PPD | 2553 ± 44(4.0) | 9107 ± 1019(6.2) |
| 65 kDa M. bovis protein | N.D | 3110 ± 645(2.1) |

REFERENCES

1. Ben-Nun, A. and I. R. Cohen. 1982. Experimental autoimmune encephalomyelitis mediated by T cell lines. I. Process of selection of lines and characteristics of the cells. *J Immunol.* 129:303.

2. Ben Nun, A. and Z. Lando. 1983. Detection of cells responding to myelin basic protein by proliferation and selection of T cell lines functional in mediating experimental autoimmune encephalomyelitis (EAE) in mice. *J. Immunol.* 130:1205.

3. Ben-Nun, A., S. Yossefi and D. Lehman. 1993. Protection against autoimmune disease by bacterial agents. II. PPD and pertussis toxin as proteins active in protecting mice against experimental autoimmune encephalomyelitis. *Eur. J. Immunol.* 23:689.

4. Hempel, K., A. Freitag, B. Enders, B. Mai and G. Leiboldt. 1985. Unresponsiveness to experimental allergic encephalomyelitis in Lewis rats pretreated with complete Freund's adjuvant. *Int. Arch. Allergy Appl. Immunol.* 76: 193.

5. Laemmli, U. K. 1970. Cleavage of structural proteins during the assembly of the head of bacteriophage T4. *Nature (Lond.).* 227:680.

6. Lehman, D. and A. Ben-Nun. 1992. Bacterial agents protect against autoimmune disease. I. Mice pre-exposed to *Bordetella pertussis* or *Mycobacterium tuberculosis* are highly refractory to induction of experimental autoimmune encephalomyelitis. *J. Autoimmun.* 5:675.

7. Lisak, R. P and M. W. Kies. 1968. Mycobacterial suppression of delayed hypersensivity in experimental allergic encephalomyelitis. *Proc. Soc. Exp. Biol. Med.* 128: 214.

8. MacPhee, I. A. M. and D. W. Mason. 1990. Studies on the refractoriness to reinduction of experimental allergic encephalomyelitis in Lewis rats that have recovered from one episode of the disease. *J Neuroimmunol.* 27: 9.

9. Matsudaira, P. 1987. Sequence from picomole quantities of proteins electroblotted onto polyvinylidene difluoride membranes. *J. Biol. Chem.* 262:10035.

10. Mehra, V., B. R. Bloom, A. C. Bajardi, C. L. Grisso, P. A. Sieling, D. Alland, J. Convit, X. Fan, S. W. Hunter, P. J. Brennan, T. H. Rea and R. L. Modlin. 1992. A major T cell antigen of Mycobacterium leprae is a 10-kD heat-shock cognate protein. *J. Exp. Med.* 175:275.

11. O'Farrell, P. H. 1975. High resolution two-dimensional electrophoresis of proteins. *J. Biol. Chem.* 250:4007.

12. Raine, C. 1984. Biology of disease. The analysis of autoimmune demyelination: its impact upon multiple sclerosis. *Lab. Invest.* 50:608.

13. Shinnick, T. M., B. B. Plikaytis, A. D. Hyche, R. M. Van Landingham and L. L. Walker. 1989. The *Mycobacterium tuberculosis* BCG-a protein has homology with the *Escherichia coli* GroES protein. *Nucl. Acids Res.* 17:1254.

14. Towbin, H., T. Staehelin and J. Gordon. 1979. Electrophoretic transfer of proteins from polyacrylamide gels to nitrocellulose sheets: procedure and some applications. *Proc. Nat. Acad. Sci. USA* 76:4350.

15. Yamaguchi, R., K. Matsuo, A. Yamazaki, S. Nagai, K. Terasaka and T. Yamada. 1988. Immunogenic protein MPB57 from *Mycobacterium bovis* BCG: molecular cloning, nucleotide sequence and expression. *FEBS Lett.* 240:115.

I claim:

1. An isolated and purified protein capable of being derived from the "Purified Protein Derivative" (PPD) of *Mycobacterium tuberculosis* (herein 12-kDa PPD protein), which protects mice against experimental autoimmune encephalomyelitis (EAE) and stimulates PPD-specific T lymphocytes, said isolated and purified protein having a molecular weight of about 12 kDa when analyzed by SDS-PAGE under reducing conditions, comprising the following amino acid sequence obtained by N-terminal analysis:

Ala-Lys-Val-Asn-Ile-Lys-Pro-Leu-Glu-Asp-Lys-Ile-Leu-Val-Gln-Ala-Asn (residues 2–18 of SEQ ID NO:1), and salts, functional derivatives and active fractions thereof which protect mice against EAE and stimulate PPD-specific T lymphocytes, and mixtures of any of the foregoing.

2. A process for producing the 12-kDa PPD protein of claim 1 comprising:

(a) fractionating PPD derived from *Mycobacterium tuberculosis* (Mt) by reverse phase high-pressure liquid chromatography (RPLC);

(b) selecting and isolating the biologically active fractions from (a) that provide highest protection of mice against experimental autoimmune encephalomyelitis (EAE);

(c) subjecting protein from the isolated fractions of (b) to RPLC and isolating the fractions having the highest protection against EAE; and (d) purifying protein from the isolated fractions of (c) by preparative gel electrophoresis, wherein said purified protein is the 12-kDa PPD protein.

3. An immunogenic composition comprising a purified protein in accordance with claim 1, and a pharmaceutically acceptable carrier.

4. An immunogenic composition according to claim 3 wherein the protein is in an amount effective for the treatment of autoimmune diseases.

5. An immunogenic composition according to claim 4 wherein protein is in an amount effective for the treatment of an autoimmune disease selected from the group comprising multiple sclerosis, rheumatoid arthritis, systemic lupus erythematosus, insulin-dependent diabetes mellitus and graft-versus-host disease.

6. An immunogenic composition according to claim 3 wherein the active ingredient is the 12-kDa PPD protein.

7. A method for the treatment of a patient afflicted with an autoimmune disease which comprises administering to said patient an effective composition whose active ingredient is a 12-kDa PPD protein of claim 1, a salt, functional derivative, or active fraction thereof or a mixture of any of the foregoing.

8. A method according to claim 7 wherein the autoimmune disease is selected from the group comprising multiple sclerosis, rheumatoid arthritis, systemic lupus erythematosus, insulin-dependent diabetes mellitus and graft-versus-host disease.

9. A method according to claim 8, wherein the autoimmune disease is multiple sclerosis.

10. A method in accordance with claim 8, wherein the active ingredient is the 12-kDa PPD protein.

* * * * *